United States Patent [19]

Atkinson et al.

[11] Patent Number: 4,519,385
[45] Date of Patent: May 28, 1985

[54] LAVAGE HANDPIECE

[75] Inventors: Robert W. Atkinson, Dover; Joseph W. Elliott; Donald W. Johnson, both of Minerva, all of Ohio

[73] Assignee: Snyder Laboratories, Inc., Dover, Ohio

[21] Appl. No.: 445,807

[22] Filed: Dec. 1, 1982

[51] Int. Cl.³ .......................... A61H 9/00; A61M 1/00
[52] U.S. Cl. .......................................... 128/66; 604/27; 604/902
[58] Field of Search ...................... 433/95, 96, 28, 101; 128/66, DIG. 12; 604/902, 22, 27, 28, 30-36, 43, 48, 73, 131, 118, 119; 137/594; 251/9, 10; 141/65, 785

[56] References Cited

U.S. PATENT DOCUMENTS

| 811,111 | 1/1906 | Wegefarth . | |
|---|---|---|---|
| 2,356,865 | 8/1947 | Mason | 251/320 |
| 2,522,261 | 9/1950 | Freedman | 32/33 |
| 2,535,310 | 12/1950 | Mattison | 251/9 |
| 2,641,087 | 6/1953 | Greiser | 51/12 |
| 2,712,323 | 7/1955 | Snyder et al. | 137/322 |
| 3,065,749 | 11/1962 | Brass | 128/224 |
| 3,109,426 | 11/1963 | Noonan et al. | 604/33 |
| 3,208,145 | 9/1965 | Truner | 32/33 |
| 3,308,825 | 3/1967 | Cruse | 128/276 |
| 3,537,444 | 11/1970 | Gara et al. | 128/66 |
| 3,540,437 | 11/1970 | Troy | 128/66 |
| 3,749,090 | 7/1973 | Stewart | 128/240 |
| 3,881,641 | 5/1975 | Pliml, Jr. et al. | 222/207 |
| 3,889,675 | 6/1975 | Stewart | 128/240 |
| 3,902,664 | 9/1975 | Deines | 239/102 |
| 3,912,168 | 10/1975 | Mullins et al. | 239/102 |
| 3,993,054 | 11/1976 | Newman | 128/66 |
| 4,036,210 | 7/1977 | Campbell et al. | 128/2 F |
| 4,097,020 | 6/1978 | Sussman | 251/10 |
| 4,193,406 | 3/1980 | Jinotti | 604/33 |
| 4,215,476 | 8/1980 | Armstrong | 433/80 |
| 4,278,078 | 7/1981 | Smith | 128/66 |
| 4,294,251 | 10/1981 | Greenwald et al. | 128/276 |
| 4,299,221 | 11/1981 | Phillips et al. | 128/276 |
| 4,350,158 | 9/1982 | Hudson | 128/224 |

FOREIGN PATENT DOCUMENTS 1586089 3/1981 United Kingdom .
1602277 11/1981 United Kingdom .

OTHER PUBLICATIONS

Ad from *Journal of Bone and Joint Surgery*, Sep. 1981, 63-A, STRYKER® SysTec ™ 280 for improved cement fixation, Stryker Corporation.

*Primary Examiner*—C. Fred Rosenbaum
*Assistant Examiner*—J. L. Kruter
*Attorney, Agent, or Firm*—Margaret L. Geringer

[57] ABSTRACT

A hand-held instrument which provides for directing irrigating fluid to a surgical site through an irrigation passage, and which may also provide for suction of fluid and debris away from the surgical site through an alternate passage. The passages are typically tubing channels which may be attached to various types of tips which are introduced at the surgical site. The handpiece instrument, including the tubing channels, may be totally disposable, or the handpiece may be adapted to allow the external housing to be reusable with only the tubing channels being disposable. Both the suction and irrigation tubing channels may be assembled internally in the handpiece housing, with both suction and irrigation being conveniently controlled with one hand by pinch valves. In an alternate embodiment, the handpiece has external mounts for attaching the suction tube, providing the operator of the handpiece the option of having the suction function attached or detached during the surgical procedure.

21 Claims, 11 Drawing Figures

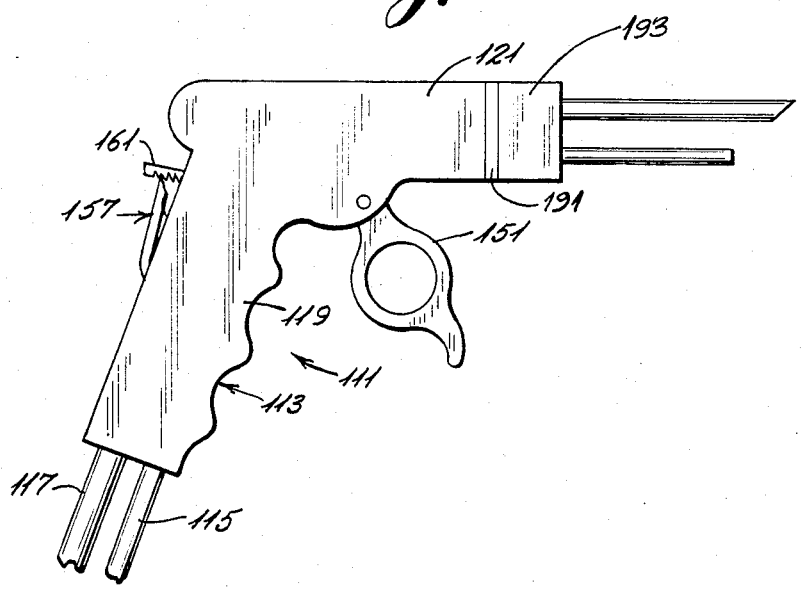
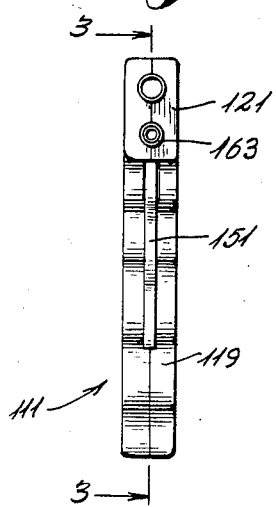
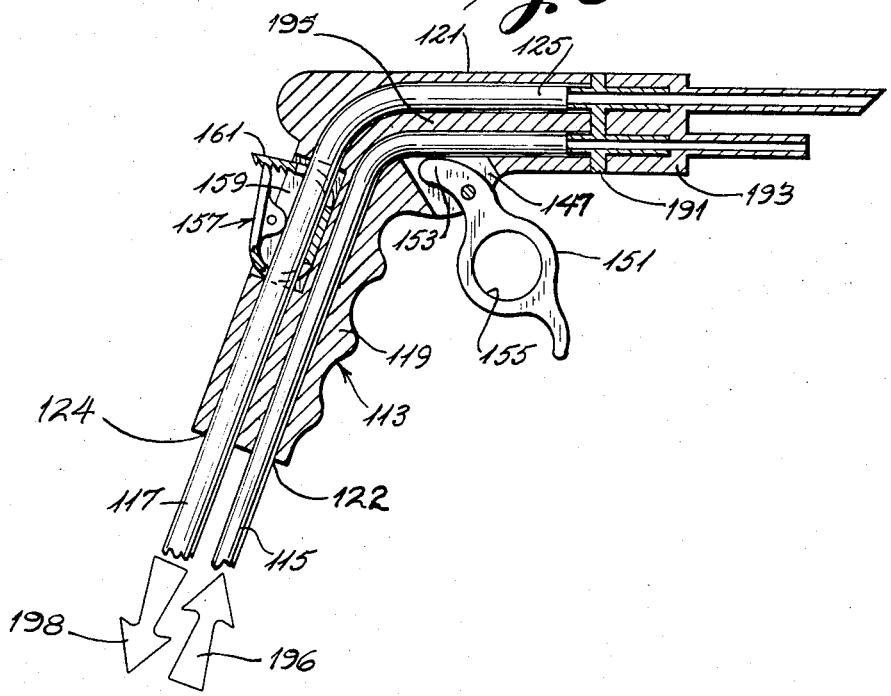

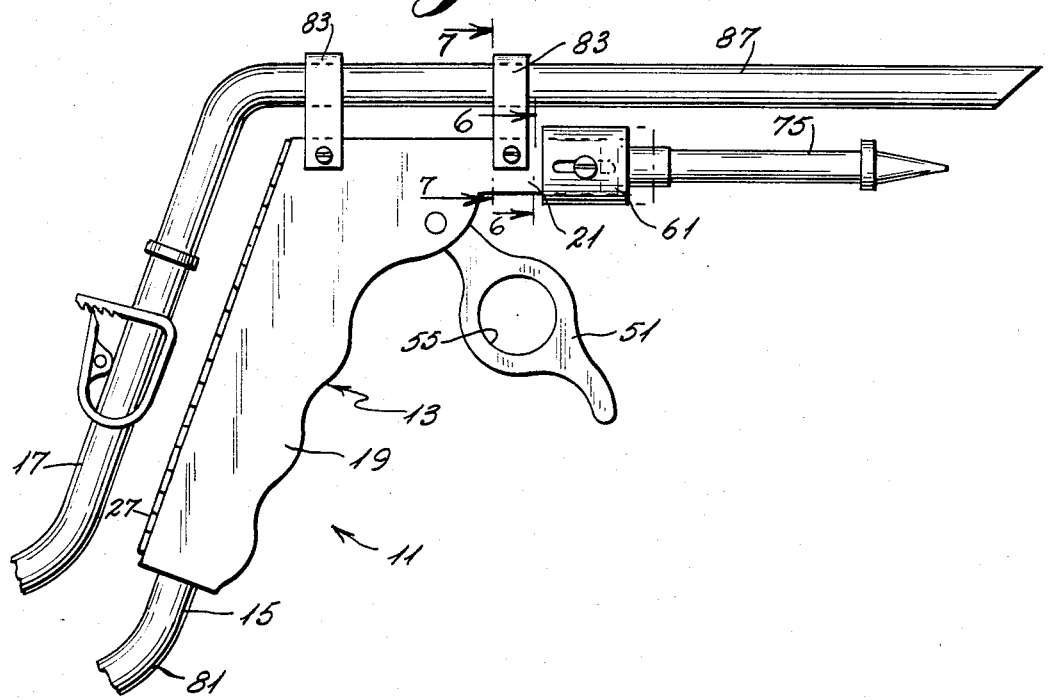
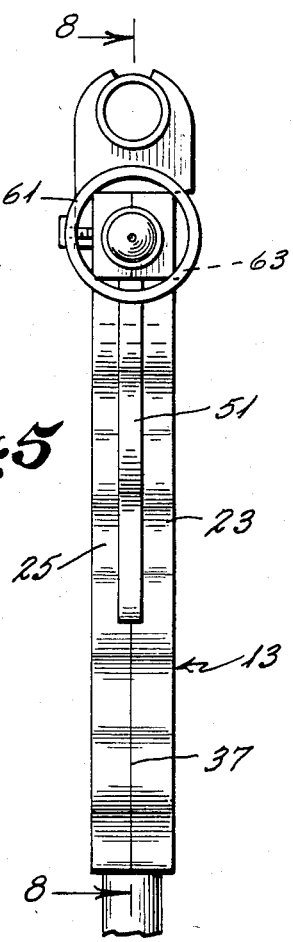
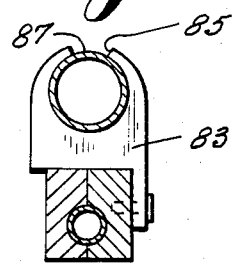

LAVAGE HANDPIECE

BACKGROUND OF THE INVENTION

The present invention generally relates to an irrigation-suction handpiece for selectively applying an irrigating fluid to, and withdrawing by suction, unwanted fluid and debris from a surgical operating site.

Hand-held irrigation suction devices have long been used in surgical and dental procedures for various purposes at the operating site or wound, to facilitate the cleaning and lavage of wounds.

Conventionally, the irrigating and suction devices have been combined in a single piece of surgical equipment for convenient hand use by the operator. One such prior art device is described in U.S. Pat. No. 4,299,221 to Earl Phillips and Robert Insalaco. This prior art handpiece provides an irrigation-suction handpiece including a handle containing longitudinally extending, side-by-side suction and irrigant passageways respectively connectible to a source of subatmospheric pressure and an irrigant fluid source. An irrigant valve is actuable for alternately opening and blocking flow of irrigant fluid from the source thereof through the irrigant passageway. An air pressure conduit includes a third passageway in the handle and connectible to an air pressure source which is not at atmospheric pressure and not influenced by pressure changes in the suction passageway. The third passageway has a portion in the handle selectively operable by the hand of the operator for effecting a change in the pressure within the third passageway. The irrigant valve has a control input coupled with the air pressure conduit and third passageway and responsive to such change in air pressure therein for shifting between its open and blocking states, to thereby control the flow of irrigant fluid to the operating site.

The third passageway contains a control hole 38. Another control opening 45 is provided which vents the suction passageway to the atmosphere. Tip suction and irrigant flow from the irrigant tip can be provided individually or simultaneously. More particularly, with the handle held in the hand of the operator, the operator may conveniently cover the hole 45 with his thumb or finger. This eliminates the bleed of air through hole 45 into suction passageway such that the full suction, generated at the handpiece by a remote vacuum source, appears at the open forward end of suction tip, for removing fluent materials from the operating site.

Alternatively, the operator's thumb or finger can be used to close hole 38 (instead of or simultaneously with its covering of hole 45). When open, the hole 38 acts as a relief for the third passageway, the gas pressure conduit and the valve control inlet, tending to keep same at near atmospheric pressure. On the other hand, closing of hole 38 causes the third passageway, the gas pressure conduit and the valve control inlet to change pressure, to the pressure of an air pressure source. This change in pressure at the control inlet opens the irrigation valve producing a flow of irrigant liquid from a source through the irrigant passageway and out the front end of the irrigant tip to the operating site.

As long as the operator of this prior art device desires irrigation and/or suction to be provided at the operative site, the operator's finger must keep the respective hole(s) covered. This restricts the hand position of the operator. Even with the suction hole uncovered, a little suction may be present at the forward end of the suction tip. Also, the irrigation valve adds unnecessary complexity to the device.

Another prior art device is described in U.S. Pat. No. 3,993,054 to Gordon Newman. This device relates to only a lavage or irrigating device. The flow of liquid is either allowed or restricted by the manual control of a pinch valve.

OBJECTS OF THE INVENTION

A principle object of this invention is to provide an irrigation-suction handpiece for surgical and dental use capable of selectively providing both suction and/or irrigation, and which provides for positive opening or shutting of the irrigation and suction channels.

Another object of the invention is to provide an irrigation-suction handpiece which permits one-handed support and convenient and comfortable one-handed control of the handpiece.

A further object of the invention is to provide a simple, easy to manufacture handpiece which may be disposable in whole or in part.

A still further object of the invention is to provide a lavage handpiece which may permit the suction channel to be detachably fixed to the outside of the handpiece so that the operator may selectively attach or detach the suction channel from the handpiece.

SUMMARY OF THE INVENTION

The present invention accomplishes all of the above objects of invention. The present invention provides a convenient hand-held assembly having a convenient and comfortable "pistol-grip" configuration. The housing provides a chamber or channel for receiving irrigation tubing. The housing may also provide a second chamber or channel for receiving suction tubing or alternatively, the suction tubing may be externally mounted on the handpiece housing so that the suction tubing may be controlled in conjunction with the handpiece, or may be separated and used separately or not at all.

A slot extends from the channel which houses the irrigation tubing. The slot supports a pinch valve for the tube. The pinch valve preferably comprises a trigger which has a portion extending so as to frictionally engage the tube, thereby enabling a flow control setting to be maintained until finger-applied force is used to change the setting. The suction tube is also provided with a hand-activated pinch valve or clamp for controlling the flow through the suction tubing. The handpiece is arranged so that control of fluid is achieved without portions of the handpiece directly communicating with the fluid.

The handpiece may be designed to provide a totally disposable handpiece or to provide a handpiece in which the housing is reuseable, but the suction and irrigation tubing is disposable.

BRIEF DESCRIPTION OF THE DRAWINGS

These features and objects of the invention, as well as others, will become apparent to those skilled in the art by referring to the accompanying drawings in which:

FIG. 1 is a side view of the lavage handpiece in accordance with the present invention;

FIG. 2 is a front view of the lavage handpiece of FIG. 1;

FIG. 3 is a sectional view of the lavage handpiece, taken along lines 3—3 of FIG. 2;

FIG. 4 is a side view of an alternate embodiment of a lavage handpiece according to the present invention;

FIG. 5 is a front view of the lavage handpiece of FIG. 4;

FIG. 6 is a sectional view taken along lines 6—6 of FIG. 4, showing a rear view of the slotted sleeve of FIG. 4;

FIG. 7 is a sectional view, taken along lines 7—7 of FIG. 4, showing a rear view of a slotted bracket of FIG. 6;

DETAILED DESCRIPTION OF THE INVENTION

Figure 8:
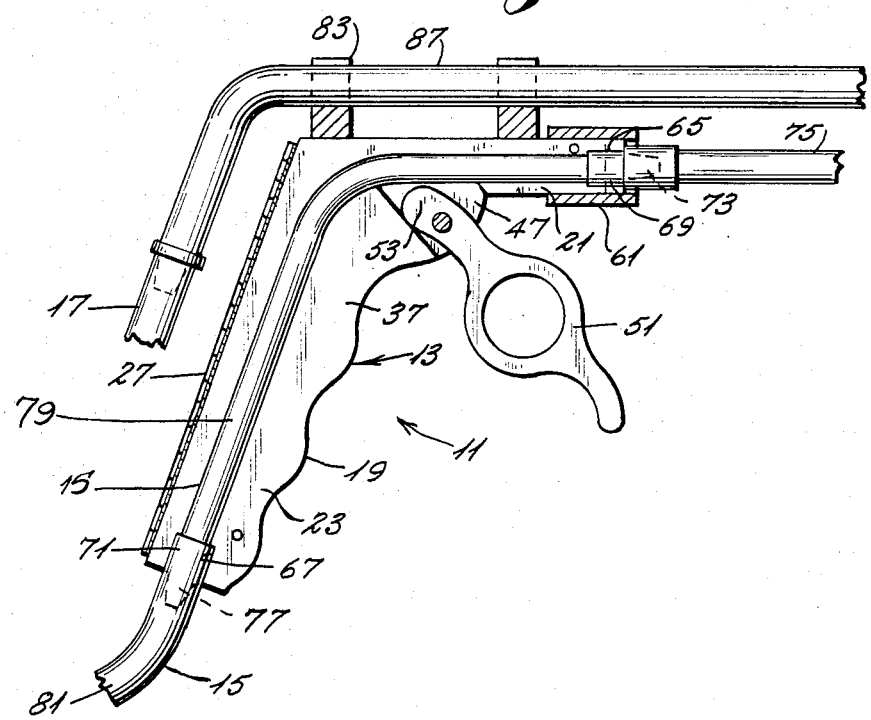
FIG. 8 is a sectional view of the lavage handpiece taken along lines 8—8 of FIG. 5.

FIGS. 1-3 illustrate a particularly advantageous embodiment of the lavage handpiece according to this invention. This handpiece 111 comprises a housing or body 113 through which irrigation and suction tubes 115 and 117 pass.

The housing 113 has a "pistol" configuration in which the housing 113 is formed with an angle so that one portion of the housing 113 is a pistol grip portion 119 which is connected with a forward facing portion 121, analogous to a pistol's muzzle. This arrangement enables an operator of the handpiece 111 to easily grip and direct the handpiece 111 while exercising convenient control of fluid flowing through the handpiece with pinch valves to be described later.

A pair of channels 122, 124 may be provided, channel 122 being an irrigation tube-receiving channel and channel 124 being a suction tube-receiving channel. The appropriate tubes pass through these channels. A slot 147 communicates between the irrigation tube-receiving channel 122 and the outside of the housing 113. A trigger 151 having tube-engaging end 153 and a finger grip 155 is pivotably mounted in slot 147. The finger grip 155 remains outside of the housing 113 so that a person holding the handpiece 111 at the pistol grip portion 119 with one hand may use a finger on that hand to use the finger grip 155 to operate the trigger 151. The tube-engaging end 153 is a cam-like projection and is located within the housing 113. The trigger 151 is pivotable so that the tube-engaging end 153 may extend into and out of the channel 122. Thus, the finger grip 155 may be used to pivot the tube-engaging end 153 into and out of engagement with an irrigation tube 115 housed by the irrigation channel 122.

The housing 113 includes a fixed internal ridge so that end 153 has a rigid surface for the trigger 151 to squeeze or wedge the tube 115 against to close off the tubing 115. When separate close fitting channels 122 and 124 are provided for tubing 115 and 117, respectfully, this portion of the housing separating the channels conveniently functions as an internal ridge 195 for the tubing to be held in place against.

When the tube-engaging end 153 is moved into engagement with the irrigation tube 115, the end 153 wedges the tube 115 against the internal ridge 153 causing the inner diameter to compress and close off. Therefore, when the trigger 151 is operated to extend into engagement with irrigation tube 115, this causes the flow to be stopped through the irrigation tube 115. The wedging action holds the end 153 in engagement against the tube 115 without the aid of externally applied pressure. When the trigger 151 is operated to pivot out of engagement with the irrigation tube 115, the appropriate irrigation flow is free to flow through the irrigation tube 115. The end of tube 115 extending from the piston-grip portion 119 is connected to an external irrigant liquid source, and the other end of the tube 115 provides an outlet means for the irrigant fluid. Arrow 196 shows the direction of the fluid flow.

In FIG. 3, the tube-engaging end 153 is shown out of engagement with the irrigation tube 115. The tube-engaging end 153 may be positioned on the trigger 151 as shown in FIG. 3 so that when the finger-grip 155 is pulled toward the pistol-grip portion 119, the tube-engaging end 153 moves into engagement with the irrigation tube 115 and shuts off the flow of irrigation through tube 115. The pistol-grip portion 119 acts as a stop means for preventing further rotation of the trigger 151.

Figure 10:
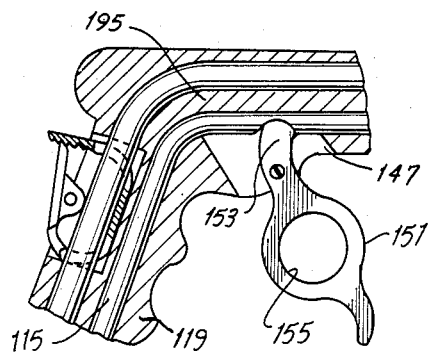
FIG. 10 is a fragmental sectional view of the lavage handpiece taken along lines 3—3 of FIG. 2, illustrating an alternate trigger embodiment.
Figure 11:
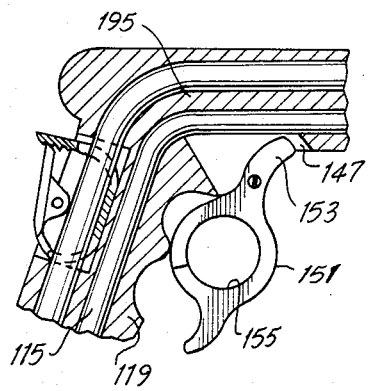
FIG. 11 is a fragmental sectional view of the lavage handpiece of FIG. 10 illustrating the trigger in a different position.

Alternatively, the tube-engaging end 153 may be positioned on the trigger 151, as shown in FIGS. 10 and 11, so that when the finger-grip 155 is pulled toward the pistol-grip portion 119, the tube-engaging end 153 disengages from the irrigation tube 115 and opens the irrigation tube 115 for flow. The first mentioned option in FIG. 3 may be referred to as the "pull-off" version, and the latter option of FIGS. 10 and 11 as the "pull-on" version. With the pull-on version, the tube-engaging end 153 is located further clockwise around the pivot of the trigger 151 so that when the finger-grip portion 155 is positioned as shown in FIG. 10, the tube-engaging end 153 is engaging and shutting off the irrigation tube 115. To disengage or open the irrigation tube 115, the "pull-on" trigger would be pulled toward the piston-grip portion 119, as shown in FIG. 11. Slot 147, as shown in FIGS. 10 and 11, is wider than that shown in FIG. 3 in order to allow the tube-engaging end 153 of the "pull-on" trigger to rotate out of engagement. Either type of trigger 151 (pull-off or pull-on) may be provided. Some operators may prefer one type of trigger action over the other.

With regard to the control of the suction function of the handpiece, a pinch valve 157 is mounted within a pinch valve opening 159, with the pinch valve opening extending from the outside of the housing 113 and interrupting the suction tube-receiving channel 124. Pinch valve 157 takes the form of a biased clip which is biased in the opened position. The pinch valve 157 includes a serrated arm 161 and a means for engaging the serrations. In order to close the suction tube 117, the means for engaging the serrations is depressed to cause a protrusion means on the valve 157 to compress or clamp off the opening in the tube 117. The fixed internal ridge 195 may also act to support the pinch valve 157 as the means for engaging the serrations is depressed. The serrated arm 161 holds the pinch valve 157 in a closed or partially closed position, as set by the operator until the serrated arm 161 is deflected, thereby releasing and opening pinch valve 157. When the suction tube 117 is open or only partially closed, suction may be provided through the suction tube 117 from a suction source which is remote from the handpiece. The end of the suction tube 117 extending from the piston-grip portion 119 is connected to the external suction source, and the other end of the tube 117 provides an inlet means for the flow of suction. Arrow 198 shows the direction of the suction flow.

Pinch valve 157 is located so that an operator may control both pinch valve 157 and trigger 151 simultaneously, probably using the thumb to control pinch valve 157 and the forefinger of the hand gripping the pistol grip portion 119 to control the trigger 151.

Various nozzle tips, such as irrigation suction nozzle tip 193 may be selectively attached to the handpiece. A nozzle adaptor 191 may be provided which attaches on one side to the suction and irrigation tubing 117 and 115, respectively. The other side of the adaptors attach to the various nozzle tips. The nozzle tips may be friction fit to the adaptor 191. Other mechanical means may be utilized if a more secure attachment is desired. The adaptor 191 may be fixedly secured to the housing 113, if desirable. The separately attachable nozzles permit the operator of the handpiece to select the type of nozzles to be used. This enables the selection of different nozzle tips and permits the changing of nozzle tips during a surgical procedure without requiring that the entire handpiece be changed. The provision of several tips provides a large selection of outputs, while eliminating a requirement that different types of handpieces be stored for different nozzle functions. The nozzles also may be disposable.

Combination irrigation and suction tips, such as irrigation nozzle tip 193 may be used. These combination tips provide a fixed relationship between the positions of the irrigation and suction nozzles. Separately attachable irrigation and suction tips may also be provided.

The housing 113 of the handpiece may be manufactured in two halves. The halves may be mechanically fixed together by screws or securing clips or other convenient means. The handpiece is readily assembled with both the suction and irrigation tubes internally fitted into the housing so that irrigation and suction are conveniently controlled by pinch valves. The separate halves conveniently allow the tubing 115 and 117 and trigger 151 and pinch valve 157 to be easily inserted in the housing 113 before securing the halves together. This feature also enables the handpiece to be reopened to replace the tubing or the trigger 151, if necessary. This enables the tubing to be disposable. It also enables the trigger 151 to be switched from a pull-off to a pull-on style or vice versa, if desirable. Alternatively, the total handpiece, including the tubing may be disposable. This configuration also minimizes assembly costs.

For the totally disposable handpiece, the housing 113 may be easily molded from any suitable plastic material. The trigger 151, the pinch valve 157, the adaptor 191, and the various nozzles may also be made of a suitable plastic material. Other materials than plastic may be used, if desired. If the handpiece housing 113 is to be reuseable, it may be more suitably manufactured from a metal material. The tubing 115 and 117 also may be any suitable material capable of being clamped off, such as PVC or silicone tubing.

Referring to FIGS. 4-9, an alternate embodiment of a lavage handpiece is shown. The handpiece 11 comprises a housing 13 through which an irrigation tube 15 passes. A suction tube 17 is mounted externally of the housing 13. The housing 13 has a piston configuration such as the previously described housing 113. The housing 13 is formed with an angle so that one portion of the housing is a pistol grip portion 19 which is connected with a forward facing portion 21. Again, this arrangement enables an operator of the handpiece 11 to easily grip and direct the handpiece 11 while exercising control of fluid flowing through the handpiece with pinch valves.

Figure 9:
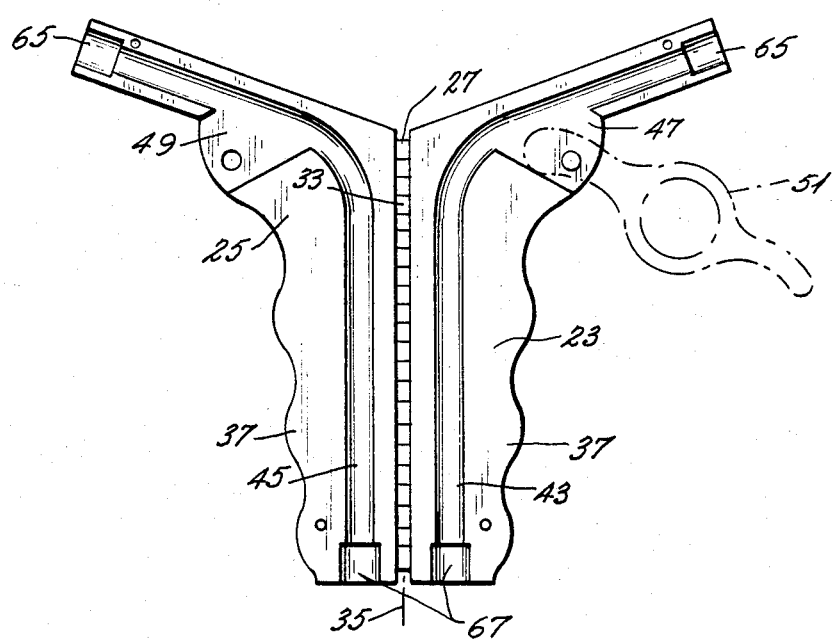
FIG. 9 is a view of the lavage handpiece body of FIG. 4 in an open position.

The housing may be manufactured in two half sections, the left half section 23 and the right half section 25 as seen in FIG. 9. The half sections 23, 25 may be linked by a flexible strip 27 or hinge portion. In the embodiment shown, the flexible strip 27 is integrally molded with the left and right half sections 23, 25. The hinge portion 27 enables the half sections to pivot about a hinge line 35 as shown in FIG. 9.

While an integral flexible hinge 27 is shown, it is anticipated that other separably attached hinge means would be suitable, if a hinge portion 27 is desirable between the half sections 23, 25. Referring to FIGS. 8 and 9, the half sections 23, 25 fall together about the hinge line 35 so that the half sections 23, 25 mate at an interface surface 37.

FIGS. 4-6 and 8 illustrate a suitable means for holding the half sections 23, 25 together. A slotted sleeve 61 is slidably mounted to the right half section 25 on the forward facing portion 21. If the sleeve is slid forward along its mount, the left half section may be closed against the right half section by passing through a side opening 63 in the slotted sleeve 61. By sliding the slotted sleeve toward the rear portion of the half sections, the sleeve 61 completely encircles a portion of both half sections 23, 25 thus cooperating with the flexible hinge 27 to lock the half sections 23, 25 in the closed position. Other suitable means for holding the half sections together may be used.

The grooves 43, 45 may be provided with enlarged ends 65, 67. One of the enlarged ends 65 is located at the forward facing portion 21 and the other enlarged end 67 is located at the pistol grip portion 19. The enlarged ends 65, 67 cooperate with enlarged portions 69, 71 on the irrigation tubing 15 to prevent the irrigation tube 15 from sliding along the grooves 43, 45. Enlarged portion 69 is a tubular flange attached to the tubing 15. The flange 69 is located at enlarged end 65 and has a tip-mounting extension 73 located thereon. The tip-mounting extension 73 extends out of the molded body 13 and forms a support for mounting interchangeable tips, such as the irrigation tip 75, to communicate with irrigation tube 15.

As shown in FIG. 8, the irrigation tube 15 is separated into a handpiece portion 79 (of the irrigation tube 15) and a main portion 81 (of the irrigation tube 15). The main portion 81 leads to the remote irrigation source. The separate main portion 81 enables the main portion to be detached from the handpiece. Typically, the complete tubing assembly, including the main portion 81 leading back to the irrigation source, would be disposable. The main portion 81 has a larger diameter than the handpiece portion 79. The larger main portion 81 fits into the enlarged end 67. An extension 77 is provided on the handpiece portion 79 to aid in attachment of the main portion 81 to the handpiece portion 79.

The left half section 23 has an irrigation tube-receiving groove 43 located at the interface 37 and extending along the length of the pistol grip portion 19 and continuing along the length of the forward facing portion 21 as shown. The right half section 25 likewise has an irrigation tube-receiving groove 45 located at the interface 37. The groove 45 on the right half section 25 is aligned to mate with the groove 43 on the left half section, so that the grooves 43, 45 form a single channel when the half sections are closed (as shown in FIGS. 4 and 5) so that the irrigation tube 15 may be housed in the channel.

Each half section 23, 25 has a slot 47, 49 respectively therein. The slots 47, 49 each extend from the groove 43 or 45 on their respective half section 23 or 25 to the exterior of the housing 13. The slots 47, 49 mate when the half sections are closed. The slots receive a trigger 51 which, when the half sections 23, 25 are closed, is pivotably mounted in the slots 47, 49. The trigger 51 has a tube-engaging end 53 and a finger grip 55. The finger grip 55 remains outside of the molded body so that a person holding the handpiece 11 at the pistol grip portion 19 with one hand may use a finger on that hand to use the finger grip 55 to operate the trigger 51. The tube-engaging end 53 is located within the housing 13 (when the half sections 23, 25 are in the closed position). The trigger 51 is pivotable so that the tube-engaging end 53 may extend into and out of the channel formed by the grooves 43, 45. Thus, the finger grip 55 may be used to pivot the trigger 51 into and out of engagement with an irrigation tube 15 housed by the irrigation tube-receiving grooves 43, 45 to control the flow of the irrigation fluid through the tubing 15.

Referring to FIGS. 4, 5 and 7, a pair of slotted brackets 83 are mounted to the right half section 25 in order to support the suction tube 17 on the housing 13. The suction tube 17 may be manually slipped into position on the slotted brackets through slots 85 so that the suction tube 17 may be selectively attached to or detached from the handpiece 11 during a surgery. Other suitable attachment means may be utilized to externally support the suction tube 17.

As shown in FIG. 4, the suction tube 17 terminates in an enlarged portion 87 which may be either flexible or rigid. If the enlarged portion 87 is rigid, then the slotted bracket 83 must be sufficiently flexible in order to permit entry of the suction tube through slot 85.

While the lavage handpiece invention has been described in terms of its preferred embodiments, those skilled in the art can appreciate that modifications can be made without departing from the spirit and scope of this invention.

We claim:

1. A medical lavage handpiece having a suction line, the handpiece comprising:
    (a) a housing having a depending grip portion and an extending forward facing portion;
    (b) a compressible irrigation tube having a first end for connecting to an external irrigant liquid source and a second end in fluid communication with said first end for providing an outlet means for the irrigant liquid;
    (c) a chamber means within the housing for receiving the irrigation tube;
    (d) a slot in the housing extending from an outer surface of the housing and communicating with said chamber; and
    (e) a manually operable trigger means for pivoting in said slot and for engaging said tube for controlling the flow of fluid in said irrigation tube,
wherein said handpiece further includes a compressible suction tube having a first end for connecting to an outside suction source, and a second end in fluid communication with said first end for providing an inlet means for the flow of suction, said suction tube including a clamping means for controlling the suction flow through the suction tube, and wherein the irrigation control trigger includes a finger gripping portion, said handpiece being operable by an operator holding the grip portion with one hand, said irrigation control trigger being operable with a finger of the one hand and said clamping means for the suction tube being operable with the thumb of the one hand, said trigger and clamping means being positioned on the handpiece to facilitate operation of both simultaneously or independently with one hand, and wherein said housing includes an external means for selectively attaching and detaching the suction tube to the outside of the housing, comprising at least one support member attached externally to said housing, the support member having a slot therein to receive the suction tube.

2. A lavage handpiece as described in claim 1, wherein said trigger includes a protruding tube-engaging means for pivoting into and out of engagement with said irrigation tube for controlling the flow of fluid in said tube.

3. A handpiece as described in claim 2, wherein the housing further includes a fixed internal ridge for the tube-engaging means to wedge the irrigation tube against.

4. A handpiece as described in claim 3, wherein the wedging is sufficient to hold the tube-engaging means in engagement with tube without the aid of externally applied pressure.

5. A handpiece as described in claim 2, wherein the tube engaging portion of the irrigation control trigger is positioned to provide engagement and closure of the irrigation tube by pulling the trigger toward the grip portion, and to provide disengagement and opening of the irrigation tube to enable fluid flow by moving the trigger away from the grip portion.

6. A handpiece as described in claim 2, wherein the tube engaging portion of the irrigation control trigger is positioned to provide disengagement and opening of the irrigation tube to enable fluid flow by pulling the trigger toward the grip portion, and to provide engagement and closure of the irrigation tube by moving the trigger away from the grip portion.

7. A handpiece as described in claim 1, wherein the trigger means further includes a means for wedging against the irrigation tube sufficient to hold the tube engaging means in engagement with the tube without the aid of externally applied pressure.

8. A handpiece as described in claim 1, wherein said handpiece further includes a stop means for limiting the pivotal rotation of the trigger means.

9. A handpiece as described in claim 1, wherein the clamping means for the suction tube comprises a pinch valve having a serrated arm and a means for engaging the serrations wherein the pinch valve may be manually closed and the serrations on the serrated arm retain the engaging means to maintain the pinch valve closed until the serrated arm is manually deflected to release the engaging means.

10. A handpiece as described in claim 1, wherein said handpiece further includes a means for the attachment of various nozzles to at least the irrigation tube at the second end of the tube.

11. A handpiece as described in claim 1, wherein handpiece further includes a means for the attachment of various nozzles to be attached to both the irrigation tube and the suction tube.

12. A handpiece as described in claim 1, wherein said housing includes a first half and a second half, said halves enabling the housing to be in an open position exposing the interior of the housing or in a closed position providing the functional position for operation of the handpiece, said housing including a suitable closure means for releasably securing the two halves together in the closed operable position.

13. A medical lavage handpiece comprising:
   (a) a housing having a grip portion and a forward facing portion;
   (b) a compressible irrigation tube having a first end for connecting to an external irrigant liquid source and a second end in fluid communication with said first end for providing an outlet means for the irrigant liquid;
   (c) a chamber means within the housing for receiving the irrigation tube;
   (d) a slot in the housing extending from an outer surface of the housing and communicating with said chamber;
   (e) a manually operable trigger means for pivoting in said slot and for engaging said tube for controlling the flow of fluid in said tube,
   wherein said housing includes a first half and a second half, said halves enabling the housing to be in an open position exposing the interior of the housing or in a closed position providing the functional position for operation of the handpiece, said housing including a suitable closure means for releasably securing the two halves together in the closed operable position, and wherein said closure means includes a hinge means connecting the first and second halves of the housing, said hinge enabling the first and second housing halves to be manually opened or closed about the hinge 14. A handpiece as described in claim 13, wherein said first and second halves of the housing are molded in one piece and said hinge is an integrally molded hinge.

15. A handpiece as described in claim 13, wherein the closure means further includes a mechanical fixation means for releasably securing the two halves together in the closed position.

16. A handpiece as described in claim 13, wherein the closure means further includes a slotted ring member being slidably mounted on one of the housing halves so that it is possible to slide the ring enabling one position of the ring to permit the housing halves to open against the hinge and enabling another position of the ring to lock the housing halves together in the closed position.

17. A lavage handpiece as described in claim 13, wherein said housing further includes a compressible suction tube having a first end for connecting to an outside suction source, and a second end in fluid communication with said first end for providing an inlet means for the flow of suction, said suction tube including a clamping means for controlling the suction flow through the suction tube.

18. A lavage handpiece as described in claim 17, wherein said housing further includes a chamber means within the housing for receiving the suction tube.

19. A lavage handpiece is described in claim 17, wherein said housing includes as external means for selectively attaching and detaching the suction tube to the outside of the handpiece.

20. A handpiece as described in claim 19, wherein the means for attaching the suction tube comprises at least one support member attached externally to the housing, the support member having a slot therein to receive the suction tube.

21. A medical lavage handpiece having a suction line, the handpiece comprising:
   (a) a housing having a depending grip portion and an extending forward facing portion;
   (b) a compressible irrigation tube having a first end for connecting to an external irrigant liquid source and a second end in fluid communication with said first end for providing an outlet means for the irrigant liquid;
   (c) a chamber means within the housing for receiving the irrigation tube;
   (d) a slot in the housing extending from an outer surface of the housing and communicating with said chamber;
   (e) a manually operable trigger means for pivoting in said slot and for engaging said tube for controlling the flow of fluid in said irrigation tube,
   (f) a compressible suction tube having a first end for connecting to an outside suction source, and a second end in fluid communication with said first end for providing an inlet means for the flow of suction;
   (g) a clamping means for controlling the suction flow through the suction tube; and
   (h) means for selectively attaching and detaching the suction tube to the outside of the housing comprising at least one support member attached externally to said housing, said support member adapted for receiving said suction tube.

* * * * *